United States Patent
Kolff et al.

[11] Patent Number: 5,976,076
[45] Date of Patent: Nov. 2, 1999

[54] STEREO LAPAROSCOPE WITH SYNCHRONIZED OPTICS

[76] Inventors: Jack Kolff, 1086 Franklin St., Johnstown, Pa. 15905; Robert Czarnek, 1450 Scalp Ave., Johnstown, Pa. 15904

[21] Appl. No.: 08/822,853

[22] Filed: Mar. 24, 1997

Related U.S. Application Data

[63] Continuation-in-part of application No. 08/392,094, Feb. 22, 1995, Pat. No. 5,613,936.

[51] Int. Cl.⁶ ........................................................ A61B 1/05
[52] U.S. Cl. .......................... 600/166; 600/111; 600/167; 600/170; 600/173
[58] Field of Search ................................... 600/111, 166, 600/167, 170, 173, 129, 130; 359/464, 471, 475; 348/45

[56] References Cited

U.S. PATENT DOCUMENTS

| | | |
|---|---|---|
| 3,329,074 | 7/1967 | Gosselin .................................. 600/111 |
| 3,520,587 | 7/1970 | Tasaki et al. . |
| 3,561,432 | 2/1971 | Yamaki . |
| 3,941,121 | 3/1976 | Olinger et al. . |
| 4,751,570 | 6/1988 | Robinson .................................. 358/88 |
| 4,873,572 | 10/1989 | Miyazaki et al. . |
| 4,877,307 | 10/1989 | Kalmanash . |
| 5,003,385 | 3/1991 | Sudo . |
| 5,059,009 | 10/1991 | McKinley . |
| 5,063,441 | 11/1991 | Lipton et al. .............................. 358/88 |
| 5,097,359 | 3/1992 | McKinley . |
| 5,119,189 | 6/1992 | Iwamoto et al. .......................... 358/88 |
| 5,122,650 | 6/1992 | McKinley . |
| 5,188,094 | 2/1993 | Adair . |
| 5,222,477 | 6/1993 | Lia . |
| 5,577,991 | 11/1996 | Akui et al. .............................. 600/111 |

FOREIGN PATENT DOCUMENTS

| | | |
|---|---|---|
| 911380 | 1/1992 | Germany . |
| 4241938 | 6/1994 | Germany . |
| 232524 | 11/1985 | Japan . |
| 4016812 | 1/1992 | Japan . |

OTHER PUBLICATIONS

The World's Only Flexible Video Laparascope, Distalvu™ 360 Video Laparascope, Welch Allyn Surgical Imagin Systems, Feb. 1995.
Stereovu™ 3D Video Laparascope, Welch Allyn Surgical Imaging Systems.
Universalvu™, Welch Allyn Surgical Imaging Systems.
3–D System With Two CCD S, Welch Allyn Surgical Imaging Systems.

*Primary Examiner*—John P. Leubecker
*Attorney, Agent, or Firm*—Clayton, Howarth & Cannon, P.C.

[57] ABSTRACT

A stereo laparoscope for producing a stereoscopic optical image of an intracorporeal region to be view through a small incision. The stereo laparoscope includes a conventional elongate tubular casing having an illuminating window and left and right observation windows disposed in a distal extremity thereof, said distal extremity for insertion within the human body. At least two separate optical imaging assemblies are disposed within the casing to produce a stereoscopic optical image. At least one of the optical imaging assemblies is moveable relative to the other. Focusing devices are synchronized with variation in depth perception to permit variation in image distance responsive to variation in depth perception.

21 Claims, 3 Drawing Sheets

STEREO LAPAROSCOPE WITH SYNCHRONIZED OPTICS

This is a continuation-in-part application of U.S. patent application Ser. No. 08/392,094, filed Feb. 22, 1995, entitled STEREO LAPAROSCOPE APPARATUS AND METHOD, now U.S. Pat. No. 5,613,936.

BACKGROUND OF THE INVENTION

1. The Field of the Invention

The present invention relates to apparatus and methods for producing a stereoscopic optical image. More particularly, the invention is directed to a stereo video laparoscope utilizing, in combination, two optical imaging assemblies, at least one of which is moveable relative to the other to vary depth perception, and with corresponding focusing adjustment of the lenses responsive to the variation in depth perception.

2. The Background Art

Modern surgeons seek to perform necessary surgical procedures on a patient while minimizing the disturbance and destruction to intervening tissues and organs. To this end, medical endoscopes have been developed as an aid to diagnostic, surgical and other medical procedures. Medical endoscopes enable visual examination of body channels, cavities, spaces and internal organs through a natural opening or small incision, and thus without conventional surgery. Medical endoscopes are also useful for visual observation during surgery. Specific endoscopes have been developed for access to various body lumens and cavities. For example, laparoscopes, bronchoscopes, sigmoidoscopes, gastroscopes, and so forth, are all available. The main difference between these devices is the size of the instrument. However, the general configuration and method of use of such scopes are quite similar. Many of the body cavities and hollow conduits (e.g. peritoneal, abdominal, bronchial, lung, esophagal, etc.) can thus be accessed through endoscopic means, without surgical incisions and the resulting trauma to the patient.

Endoscopes typically include a long, thin tubular casing optically connected to a viewing mechanism. The tubular casing is narrow enough to insert through a small natural or surgical opening in the body. When the endoscope is inserted and positioned for use, an image of the object being viewed is formed at an inserted end thereof by an objective lens. The image is passed through a series of relay lenses down the cylinder to an eye lens or video camera at a viewing end of the endoscope. A major drawback to using an endoscope as a surgical aid is that it gives a monocular view and therefore no depth perception. Surgical procedures such as suction, irrigation, biopsy, incisions, suturing and cutting must be learned without the benefit of three dimensional visualization.

Endoscopes have recently been developed which produce the illusion of three dimensions or depth by combining two dimensional images. However, the mechanics of providing such a stereoscopic or three dimensional view require an increase in the size, weight and/or number of endoscopes, thus adding to the problem of limited portal entry space and convenience.

The stereoscopic effect is created by producing two optical images of the desired region, each image having a different point of view, such as a left image and a right image. It is known to incorporate two separate optical fiber bundles in parallel inside a single casing to add the advantages of fiberoptics to stereoscopic viewing. The two images are carried by the two optical fiber bundles, respectively, to left and right image sensors, which may comprise charge-coupled device (CCD) cameras or other image sensing devices. The sensing devices convert the left and right optical images into left and right video images, respectively. The video images are then presented as alternating left-right images on a viewing monitor to the user to thereby create a stereoscopic or three-dimensional optical view.

Although prior art endoscopes have succeeded in producing a stereoscopic or three dimensional effect, they are characterized by a number of disadvantages. The known stereoscopic instruments are not designed to give good stereoscopic viewing inside the larger body cavities such as the pleural and peritoneal cavities. Moreover, they lack adequate depth perception variability.

OBJECTS AND SUMMARY OF THE INVENTION

It is therefore an object of the present invention to provide an improved stereo endoscope for producing a stereoscopic optical image of an intracorporeal region of the human body.

It is an additional object of the invention to provide such a stereo endoscope which provides synchronized variation in depth perception and focusing.

It is also an object of the invention to provide such a stereo endoscope which offers a high quality optical image but which is also economical.

It is still another object of the invention to provide such a stereo endoscope which is well suited for inspecting the larger body cavities.

The present invention is described in terms of a laparoscope to be used in inspecting intracorporeal regions of the human body, such as the peritoneal or abdominal cavities, during diagnostic, surgical or other medical procedures. However, it is to be understood that the principles of the present invention may be used in any medical endoscope, such as the thoracoscope, or in any other field of stereoscopic optical imaging. For example, in the industrial field, an industrial endoscope is used to inspect structures, components, damaged areas and the like in spaces which are relatively inaccessible, such as a damaged portion of the inner wall of a pipe or the interior of a jet engine. Those having ordinary skill in the field of this invention will appreciate the advantages of the invention, and its broad application to the general field of stereoscopic image production within spaces of limited size.

The above objects and others not specifically recited are realized in a specific illustrative embodiment of a stereo laparoscope apparatus for producing the illusion of a stereoscopic or three dimensional view of the abdominal cavity through a small incision. The stereo laparoscope includes a conventional elongate tubular casing having an illuminating window and left and right observation windows disposed in a distal extremity thereof, said distal extremity for insertion within the human body. At least two separate optical imaging assemblies are disposed within the casing to produce a stereoscopic optical image. At least one of the optical imaging assemblies is moveable relative to the other. Focusing devices are synchronized with variation in depth perception to permit variation in image distance responsive to variation in depth perception.

The embodiment of the invention as a surgical instrument is merely illustrative, and does not limit the scope of the present invention. For example, the invention may be applied to extend optical vision to any context or space where it desired that human contact therewith be avoided, such as in radioactive environments, in space or in deep sea applications. Any suitable size or configuration of the invention may be employed, and the optical imaging assemblies may in some applications be spaced six feet apart, for example.

In use, a physician makes a small incision in the abdominal cavity and inserts the distal end of the laparoscope therein so that said distal end resides within the abdominal cavity at a desired location. The physician can then inspect the location by viewing the three dimensional video image thereof displayed by specialized glasses, maneuvering the laparoscope as desired in order to achieve an optimal view.

The combination of a relay means with a single fiber bundle may be utilized, if desired, to produce a stereoscopic or three dimensional image having resolution and image quality just as keen as that produced by a laparoscope utilizing two optical fiber bundles of the same quality. The resulting compactness and relative light weight of the laparoscope due to the elimination of a second image receiver, one of the cameras and corresponding cables, makes it easier for the physician to maneuver the laparoscope which, under the press of surgery and other medical procedures, helps make the procedure more effective.

BRIEF DESCRIPTION OF THE DRAWINGS

The above and other objects, features and advantages of the invention will become apparent from a consideration of the subsequent detailed description presented in connection with the accompanying drawings in which.

Figure 1:
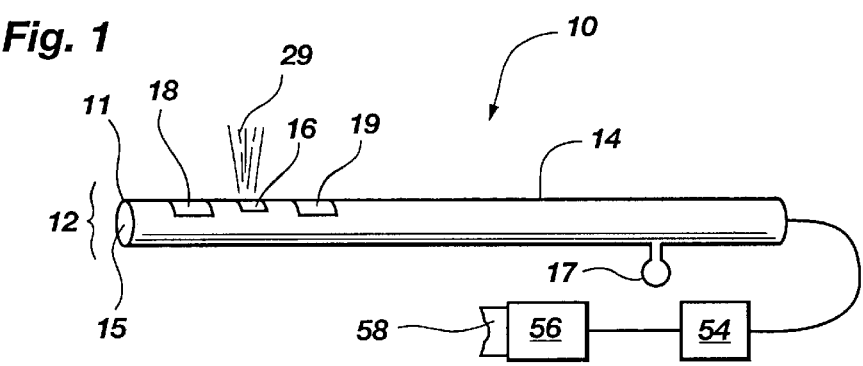
FIG. 1 is a perspective view of a stereo laparoscope made in accordance with the principles of the present invention.

DETAILED DESCRIPTION OF THE PRESENTLY PREFERRED EMBODIMENTS OF THE PRESENT INVENTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated apparatus, and any additional applications of the principles of the invention as illustrated herein, which would normally occur to one skilled in the relevant art and possessed of this disclosure, are to be considered within the scope of the invention claimed.

Applicants have discovered a new design concept for producing a stereoscopic image of intracorporeal objects with a laparoscope. Principal aspects of the present invention include special optics capable of producing variably depth perception, and synchronized focusing of left and right images in tandem with variation in depth perception.

Figure 6:
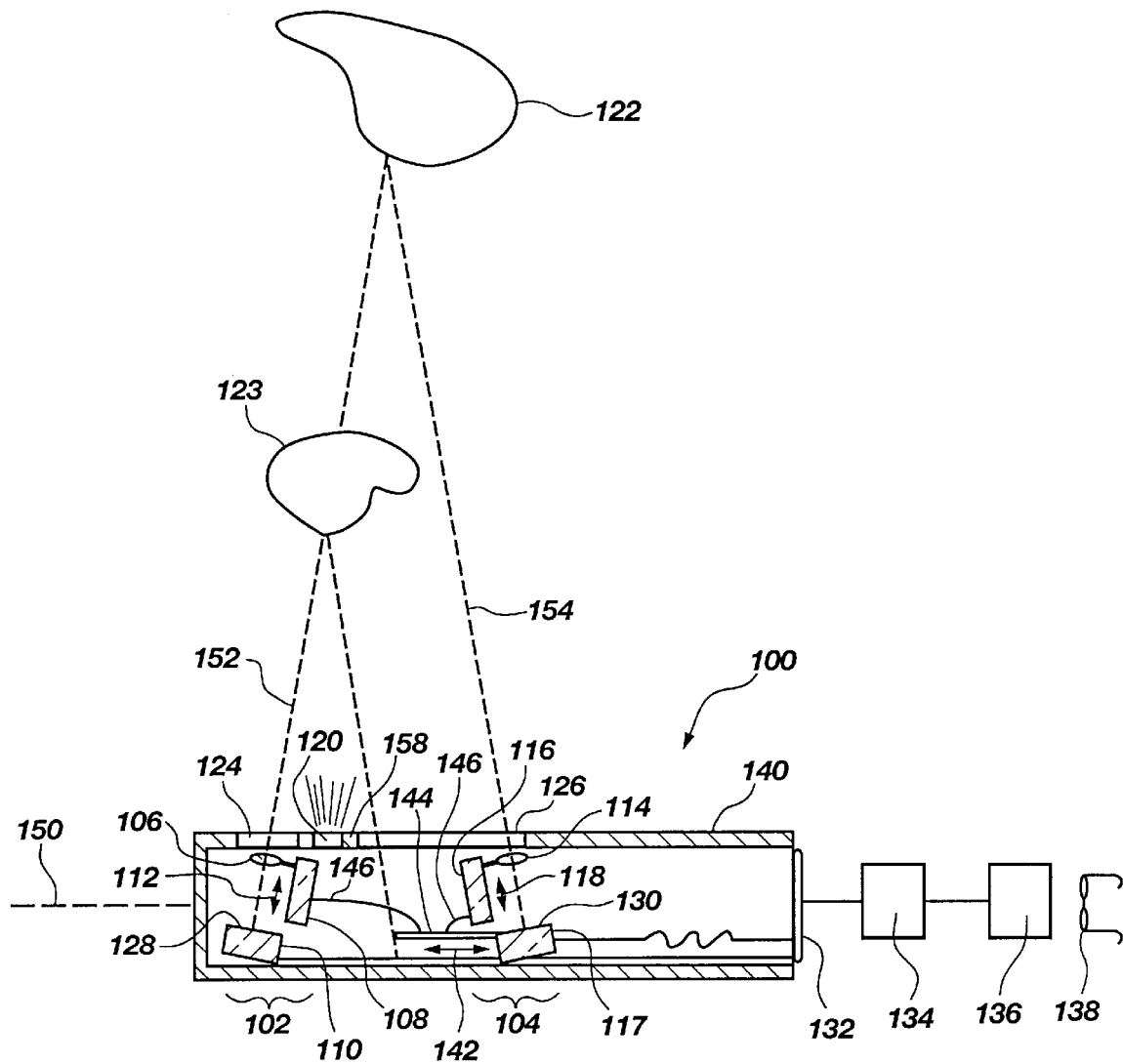
FIG. 6 is a side, cross sectional view of a further embodiment of a stereo laparoscope, made in accordance with the principles of the present invention.

Referring now to FIG. 6, there is shown a stereo laparoscope, designated generally at 100. The laparoscope includes a first imaging assembly 102, and a second imaging assembly 104. The first imaging assembly 102 includes an objective lens 106, and a first focusing means 108 for moving the lens 106 toward and away from an image receiver 110, as indicated by arrow 112. Similarly, the second imaging assembly 104 includes an objective lens 114, and a second focusing means 116 for moving the lens 114 toward and away from an image receiver 117, as indicated by arrow 118.

When the laparoscope 100 is placed within a body, such as through a surgical incision, a lamp 120 is used to illuminate an intracorporeal region 122. Light reflected from the intracorporeal region 122 is received through first and second openings 124 and 126, and is processed by the lenses 106 and 114 into left and right optical images, respectively. The left and right optical images are then received at image planes 128 and 130, respectively, of the image receivers 110 and 117, respectively. The image receivers 110 and 117, which might illustratively comprises CCD camera chips as known in the art, then convey the images to a camera apparatus 134 that is optically connected to the image receivers 110 and 117 by optical connecting structure 132. The camera apparatus 134 then passes the images to any suitable displaying means for displaying the images as a stereoscopic image, such as monitor 136 and viewing glasses 138. The glasses 138 may comprise CrystalEyes™ glasses.

The first and second openings 124 and 126 preferably comprise left and right windows formed in sidewalls of a casing 140 of the laparoscope 100. The second opening 126 is substantially wider than the first opening 124, as shown in FIG. 6, in order to accommodate movement of the second imaging assembly 104 toward and away from the first imaging assembly 102, as indicated by arrow 142. The movement of the second imaging assembly 104 produces variation in depth perception. The phrase "depth perception" as used herein refers to the ratio of the separation distance between the lenses 106 and 114 to the distance of the intracorporeal region 122 to the lenses 106 and 114. The distances of the intracorporeal regions 122 to the lenses 106 and 114 are preferably substantially the same.

The movement of second imaging assembly 104 is accomplished by a moving means 144 for moving said second imaging assembly 104. The first and second focusing means 108 and 116 are preferably operatively connected to the moving means 144 as indicated by connectors 146, such that said first and second focusing means 108 and 116 and said moving means 144 collectively comprise a synchronizing means for simultaneously varying (i) the depth perception of the stereoscopic optical image, and (ii) the focus of the left and right optical images.

More preferably, the first and second focusing means 108 and 116 and the moving means 144 comprise automated control means for varying the focus of the left and right optical images responsive to variation in the separation distance between the lenses 106 and 114. For example, the automated control means may comprise an electro-mechanical means for producing an electrical signal corresponding to variation in the separation distance between the lenses 106 and 114, and the electrical signal is passed through the connectors 146 to the focusing means 108 and 116, which operate to vary the focus of the left and right optical images responsive to said electrical signal.

It is to be understood that each lens 106 and 114 has a focal length, as that optical parameter is understood by those having ordinary skill in the relevant art. The synchronizing means, which includes the focusing means 108 and 116 and moving means 144, further comprises means for varying the depth perception and focus, such as a suitable microprocessor contained in the moving means 144 or in some other location, to thereby substantially maintain a mathematical relationship as follows:

$$1/f_1 = 1/l_1 + 1/l_2,$$

where $f_1$=the focal length of the lenses, $l_1$=working distance, defined as a distance between the lenses 106 and 114 and the intracorporeal region 122, and $l_2$=image distance, defined as a distance between a lens and an image plane, such as the distance between the lens 106 and the image plane 128.

The casing 140 comprises an elongate casing having sidewalls defining an axial direction 150. At least the first observation opening 124 and the second observation opening 126 are formed in said sidewalls. The first lens 106 defines a first optical axis 152, and the second lens 114 defines a second optical axis 154. The first and second lenses 106 and 114 are disposed to face the first and second observation openings 124 and 126, respectively, such that the first and second optical axes 152 and 154 extend transversely with respect to the axial direction 150 of the casing 140. The first image receiver 110 is disposed in alignment with the first lens 106 and the second image receiver 117 is disposed in alignment with the second lens 114.

The synchronizing means as described above may be further described as a means for (i) moving the lenses 106 and 114 in a substantially parallel direction relative to the axial direction 150 of the casing 140, and (ii) moving the lenses 106 and 114 in a transverse direction relative to the axial direction 150 of the casing 140, and thus toward and away from the image receivers 110 and 117. The synchronizing means thus varies the separation distance between the lenses 106 and 114 responsive to variation in the working distance (distance between incorporeal region 122 and lenses 106, 114), in a manner sufficient to maintain a substantially constant ratio of working distance to separation distance. For example, if the laparoscope 100 is focused upon the intracorporeal region 122 and is then moved to focus upon a closer intracorporeal region 123, the moving means 144 would operate responsively to reduce the separation distance between the lenses 106 and 114. Preferably, the lenses 106 and 114 are positioned and arranged such that their optical axes 152 and 154 coincide substantially at the intracorporeal region 122 to thereby define an acute angle as shown in FIG. 6.

It will be appreciated that the moving means 144 comprises a variable depth perception means for moving one of the optical imaging assemblies 102 and 104 relative to the other image processing assembly. The laparoscope may thereby be designed such that either of the optical imaging assemblies 102 and 104 is moveable. The moving means 144 is preferably an electro-mechanical device, and may comprise a suitable software processing means for its operation. Alternatively, the moving means 144 may comprise a manually operable means for moving one of the optical imaging assemblies 102 and 104 relative to the other optical image assembly.

The laparoscope 100 may be equipped with a sensing means 158 for (i) measuring a working distance, said working distance being defined as a distance between a lens and the intracorporeal region, and (ii) generating a signal corresponding to said working distance. The moving means 144 would then further comprise a suitable means responsive to the signal for varying the separation distance in a manner sufficient to maintain a substantially constant ratio of working distance to separation distance.

The image receivers 110 and 117 constitute an image receiving means, and are preferably CCD camera chips but may also comprise first and second optical fiber bundles. Alternatively, the image receivers 110 and 117 may be replaced with a single optical fiber bundle which receives both left and right optical images in an alternating manner, with the aid of suitably placed reflective means and optical switching technology, as well as any related optical necessities such as magnification means, as this alternative design is understood by those having ordinary skill in the art, and in reference to the further disclosure below.

In accordance with the disclosure above, a preferred method of producing a stereoscopic optical image of an intracorporeal region comprises the steps of:

(a) inserting a casement into a body and illuminating the intracorporeal region to thereby cause said region to reflect light;

(b) processing light reflected from the intracorporeal region into left and right optical images and transmitting said optical images within the casement to an image receiving means disposed within said casement;

(c) transmitting said optical images to an output display to thereby produce a stereoscopic optical image of the intracorporeal region on said output display; and (d) varying depth perception of the stereoscopic optical image.

An alternative embodiment of a stereo laparoscope having fixed focus imaging and fixed depth perception is illustrated in FIG. 1. Referring to FIG. 1, there is shown a stereo laparoscope, generally designated at 10, for inserting into the abdominal cavity through a small incision. The stereo laparoscope 10 comprises a hollow, elongate casing designated by bracket 12 having cylindrical side walls 14. An illuminating window 16 and left and right observation windows 18 and 19, respectively, are disposed in the side walls 14, preferably near distal extremity 11. A side mounted handle grip 17 for gripping by the user provides a natural feel.

Figure 2:
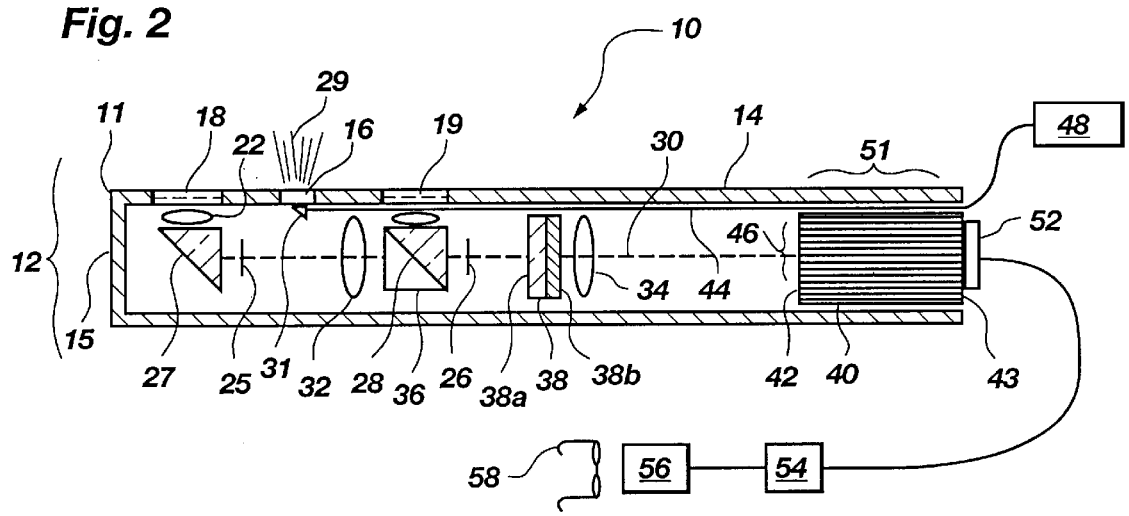
FIG. 2 is a side, cross sectional view of the stereo laparoscope of FIG. 1.

Referring to FIG. 2, there is shown a side, cross sectional view of the laparoscope 10, of FIG. 1. The laparoscope 10 further includes left and right objective lenses 22 and 23, and left and right mirrors 27 and 28, respectively. First and second image planes 25 and 26 lie along a common line of sight 30, as do stationary imaging lens 32, stationary focusing lens 34, polarizing beam splitter 36, optical switch 38, and the left and right mirrors 27 and 28. It can be seen in FIG. 2 that left and right mirrors 27 and 28 are diagonally positioned with respect to the common line of sight 30. A coherent, image-transmitting optical fiber bundle 40 having first and second opposite end faces 42 and 43, respectively, is also disposed within the casing 12. The first and second end faces 42 and 43 include image-receiving and image-transmitting fiber tips, respectively, the image-receiving tips being shown at bracket 46. The bundle 40 is coherent in that the opposing tips of each fiber are located in substantially exactly the same positional orientation within the end faces 42 and 43, respectively, to prevent scrambling and distortion of the transmitting image. Light-emitting fibers 44 are disposed within the casing 12 and in contact with a prism 31, for providing light 29.

A preferred casing comprises a thin, elongate casing body 12 having a front-end face 15 and cylindrical walls 14. The portion of the casing 12 between the front-end face 15 and the first face 42 of the fiber bundle 40 must be rigid to maintain precise positioning of the imaging optics therein. The portion of the casing 12 containing the bundle 40 may be made from a soft, semi-rigid material so that it can be flexed and more easily inserted through irregular passages. The casing may alternatively comprise any cross sectional shape or material suitable for intracorporeal insertion and for housing the assembly to be contained therein.

The fiber bundle 40 comprises several hundred thousand image-transmitting fibers 46 each having a diameter of about 5 to 10 microns. The resolution of an image carried by the fiber bundle 40 is a function of the number of fibers present. At the present time, each fiber must be at least about five to ten microns in diameter in order to prevent light from escaping from the fiber. This minimum diameter requirement on the fibers, coupled with the number of fibers necessary to convey a high-quality optical image, necessitates a fiber bundle 40 having a diameter of approximately ten millimeters, and hence the casing 12 is approximately twelve millimeters in diameter. It is expected that these dimensions will decrease with time as the technology advances. However, any such dimensional limitations render the single-bundle arrangement discovered by the applicants advantageous relative to the two-bundle systems.

According to applicant's present knowledge, rigid fiber bundles offer image quality superior to that offered by flexible fiber bundles. The fibers 46 comprise a multi-compound glass fiber having an inner core for carrying light and outer cladding for keeping the light within the core. This is accomplished by using cladding which has a different index of refraction than the core material, thereby creating a light guide. The core has a higher index of refraction than the cladding. However, the fiber bundle 40 may alternatively comprise flexible fibers of multi-compound plastic, or any other optical fiber which would facilitate the purposes of the present invention.

The first and second end faces 42 and 43 comprise the tips of the coherent bundle of fibers 40. The fibers 46 are tightly fused together by their cladding at the first and second end faces 42 and 43 so that the same positional relationship of the fibers is maintained at said faces. The fibers preferably remain loose in the middle section, designated at bracket 51, but this is not required. The light-emitting fibers 44 may comprise a silicone resin, a multifiliment type plastic optical fiber or any other fibrous material suitable for transmitting light. The light-emitting fibers 44 may be spatially separated from the fiber bundle 40 as shown in FIG. 2, or may alternatively be mounted upon the bundle 40 or even incorporated within the bundle 40 itself, and will preferably comprise a bundle having a diameter of approximately one millimeter or less.

A fiberoptic light source 48 comprising an arc lamp is connected to the light-emitting fibers 44 for introducing light therein. The light source 48 may alternatively comprise a halogen lamp or any other light source suitable for introducing light into fiberoptic filaments. When the light source 48 is actuated, light is introduced into the fibers 44 which carry the light to the prism 31. The light 29 is reflected by prism 31 and thereby projected through the illuminating window 16, or may alternatively be so conveyed in any manner known to those skilled in the art. The light 29 then illuminates an object or region (not shown) external to the laparoscope 10 to thereby cause said external object to reflect light. The light reflected from the external object enables the left and right observation windows 18 and 19 to provide left-hand and right-hand points of view of said external object.

The left-hand point of view is processed by the left objective lens 22 into a left optical image. The left optical image is transmitted onto the first image plane 25 by the left mirror 27. Similarly, the right observation window 19 provides access to a right-hand point of view which is processed by the right objective lens 23 into a right optical image and transmitted onto the second image plane 26 by the right mirror 28. Both objective lenses 22 and 23 preferably have the same aperture and focal length.

The left and right mirrors 27 and 28 are positioned so that they project their respective images substantially along the common line of sight 30 such that they are superimposed upon second image plane 26. The left optical image from the first image plane 25 is collected by the stationary imaging lens 32 and projected onto the second image plane 26 with magnification so that the left and right optical images have substantially the same magnification when they are superimposed on second image plane 26. Both images pass through the polarizing beam splitter 36 in such a way that both images have opposing polarity. The optical switch 38 collects the left and right polarized optical images and alternately transmits them, i.e. one-at-a-time, onto the image-transmitting fibers 46 of the first end face 42 of the fiber bundle 40. The optical switch 38 includes a liquid crystal polarization rotator 38a and a linear polarizer 38b which operate as known in the art to accomplish the alternating transmission of the left and right polarized optical images. The image-transmitting fibers 46 carry the alternating left and right polarized optical images to the second end face 43.

The optical switch 38 preferably comprises a liquid crystal layer and is known in the art for the capacity to alternately block and transmit horizontally and vertically polarized images. The purpose of polarizing the two optical images is thus to allow the optical switch 38 to transmit the left and right images one at a time to the first end face 42 of the fiber bundle 40. The purpose of having a left image and a right image is to provide an optical image having depth, or the illusion of three dimensions.

Variable focusing can be achieved by causing the focusing lens 34 to be moveable along the line of sight 30 as will be described later in more detail. For fixed focus imaging, the focusing lens 34 can be fixed or eliminated.

A camera apparatus 54 is optically connected to the image-transmitting fibers 46 at the second end face 43, said connection represented by connecting structure 52. The camera receives the alternating left and right optical images from the second end face 43 in tandem with the optical switch 38 at said predetermined rate. The camera 54 presents the images as enlarged, alternating left-right video images on a monitor 56 shown schematically in FIG. 2. The monitor displays the alternating images and the surgeon wears specialized glasses 58 having optical valves, such as Crystal-Eyes™ glasses, to view the alternating images on the monitor 56.

The glasses 58 are simply two optical valves or shutters that transmit the images one at a time alternately to the left eye and the right eye in tandem with the optical switch 38 and monitor 56 at said predetermined rate. The predetermined rate of alternation is preferably controlled by a scan signal from the monitor 56, which controls the optical switch 38 in the stereo laparoscope and the optical valves in the glasses 58 with conventional video circuitry. This arrangement ensures that the optical switch, camera, monitor and optical valves operate in tandem and at the same rate. Thus, the left eye sees only images from the left observation window 18 of the endoscope and the right eye sees only images from the right observation window 19, creating a stereoscopic view. The rate of alternation is faster than the flicker-sensing limit of the human eye, resulting in flicker free viewing.

A unique aspect of the present invention is that the observation windows 18 and 19 are disposed in the side walls 14 of the casing 12 instead of in the front-end face 15. This window arrangement advantageously allows a user to position the side walls 14 adjacent to a desired intracorporeal viewing region for a transverse view, instead of requiring the front-end face 15 to face the viewing region. The transverse viewing arrangement also allows for a larger separation of distance between the windows 18 and 19 and associated lenses, while maintaining a smaller diameter of the housing 12. The window arrangement of the present invention thereby makes it easier for the user to view relatively remote intracorporeal regions, with a minimum of disturbance to surrounding tissue and organs.

Figure 4:
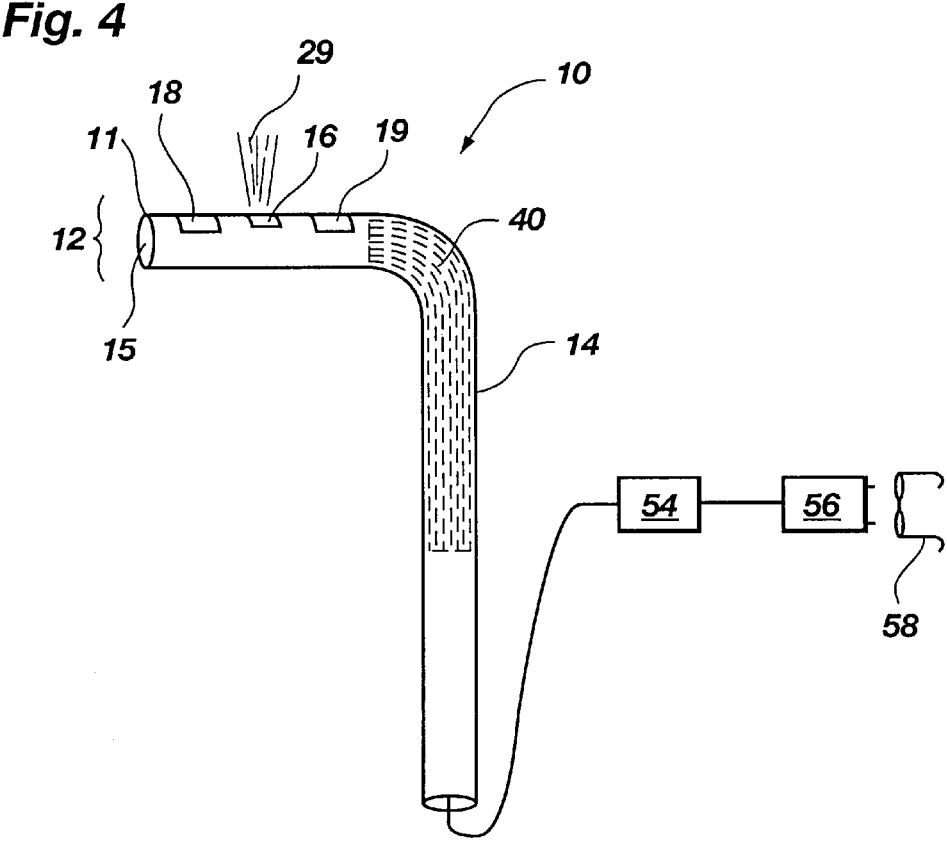
FIG. 4 is a perspective view of another alternative embodiment of the stereo laparoscope of FIG. 1 with an optical fiber bundle shown in phantom.

The embodiment presented in FIG. 2 illustrates the simplest embodiment, namely, a stereo laparoscope 10 comprising a rigid or semi-rigid straight casing 12 allowing observations at the right angle. However, the laparoscope may alternatively comprise a rigid or semi-rigid casing 14 bent at a 90 degree angle as shown in FIG. 4. As noted above, at least the portion of the casing 12 between the front-end face 15 and the fiber bundle 40 must be rigid in order to maintain precise positioning of the imaging optics therein. The embodiment of FIG. 4 allows for a straight forward observation while utilizing the fiberoptic advantage of transmitting an image around curves by using a curved fiber bundle, illustrated in phantom at 40 in FIG. 4. It is also within the scope of the present invention to use a flexible casing with a flexible fiber bundle to allow the physician to selectively flex the laparoscope in order to achieve a desired point of view.

The observation windows 18 and 19 are preferably arranged substantially in a row along the hollow casing 12, but may alternatively be arranged in some other configuration. Said observation windows may alternatively comprise three or more observation windows. The illuminating window 16 is lined up in the row with the observation windows 18 and 19, but may be arranged otherwise and may alternatively comprise two or more illuminating windows.

The most economical embodiment utilizes a single optical switch 38 positioned in the common line of sight 30 of two beams of light, as discussed above in conjunction with FIG. 2. However, the same effect could be accomplished with two separate light valves, one for each observation window 18 and 19, but at a higher cost. This alternative configuration offers improved contrast, and is discussed below in conjunction with FIG. 5.

Instead of using left and right objective lenses 22 and 23 to process the light into left and right optical images, optical imaging properties may be incorporated into the left and right observation windows 18 and 19. In this configuration, said windows 18 and 19 would serve the dual purpose of receiving the light reflected from an external object to be viewed, and processing the light received into left and right optical images. All lenses (i.e. objective lenses, imaging lenses, focusing lenses, and so forth) have been presented as single element components. However, the scope of the invention includes multi-element lenses as are known in the art for improving the image quality and otherwise optimizing the performance of the system.

The mirrors 27 and 28 and the beam splitter 36 have been presented in FIG. 2 in the form of prisms and a cube, respectively. The mirror 28 is actually a surface of the beam splitter 36. This is a preferred configuration. However, plane front surface mirrors and a flat beam splitter could be used without changing the basic concept of the invention.

The means for alternating the left and right optical images may also comprise apparatus other than the optical switch 38. For example, the observation windows 18 and 19 may comprise liquid crystal display (LCD), shutter-type windows designed to alternately block and receive light, or other windows which can be so designed. The shutter-type window element is shown schematically in FIG. 3 as phantom lines 18a and 19a. Such shutter-type windows essentially turn on and off as known in the art to alternately block and receive light. Electronic switching means would cause the windows to alternately block and receive light at a predetermined rate such that the left observation window 18 receives light while the right observation window 19 blocks light, and vice versa. The optical switch 38 would be unnecessary in this case. Other alternative embodiments include separate left and right polarizers, shown schematically in phantom line as items 36a and 36b in FIG. 1, for processing the light received from the left and right observation windows 18 and 19, respectively, into left and right polarized images of the intracorporeal region, with the images having opposing polarity, in lieu of the polarizing beam splitter 36.

Fixed focus optics are suitable for many applications of stereoscopic imaging, wherein the focusing lens 34 remains in a stationary position. However, adjustable focus is a useful feature for many of the demands of surgery and other medical procedures. Adjustable focus may be provided for the embodiment of FIG. 2 by designing the focusing lens 34 to be moveable along the line of sight 30 using mechanical or electrical remote control as is known in the art. The focus of the stereoscopic optical image produced by the laparoscope 10 would vary with variation of the movement of said focusing lens along the line of sight 30. Means for adjusting the focus may alternatively be implemented by translating the fiber bundle 40 along the line of sight 30 by manual or remote control.

Figure 3:
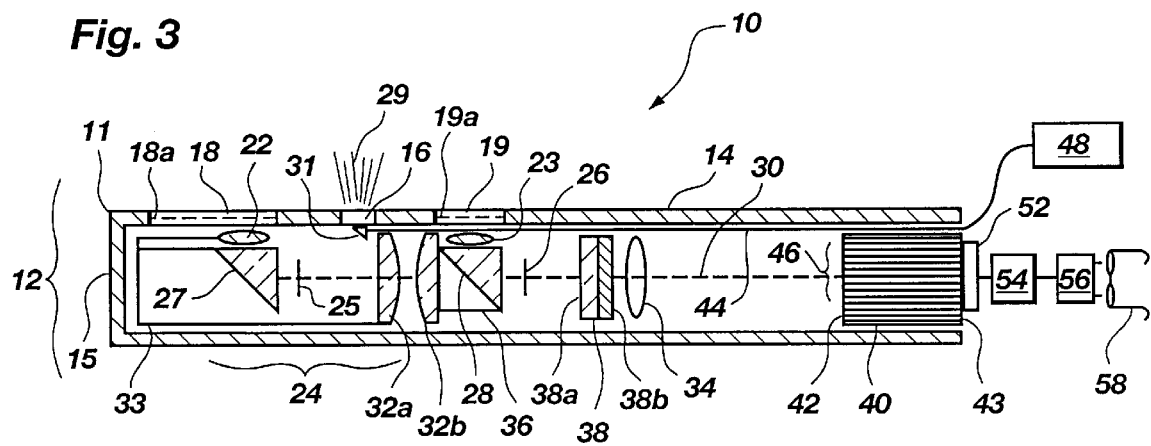
FIG. 3 is a side, cross sectional view of an alternative embodiment of the stereo laparoscope of FIG. 1.

The depth perception of the embodiment illustrated in FIG. 2 is non-variable since the left and right objective lenses 22 and 23 remain stationary and the distance therebetween is thus constant. In many applications this is sufficient. However, variable depth perception is desirable in some cases. This is achieved by a modification to the embodiment of FIG. 2, illustrated in FIG. 3. FIG. 3 shows a preferred embodiment of a stereo laparoscope which provides variable depth perception by essentially splitting the imaging lens 32 of FIG. 2 into two separate lenses. A moving assembly designated by bracket 24 comprises movable left objective lens 22, movable left mirror 27 and movable imaging lens 32a. The left observation window 18 is enlarged to accommodate the movement of the left objective lens 22. Imaging lens 32b is stationary. The left objective lens 22, the left mirror 27, and the imaging lens 32a move in tandem as a unit by means of mechanical or electrical remote control as is known in the art. A means for moving these elements in tandem is shown schematically in FIG. 3 as item 33. By translating the moving assembly 24 along the line of sight 30 as such, a stereoscopic optical image having variable depth perception is achieved.

Figure 5:
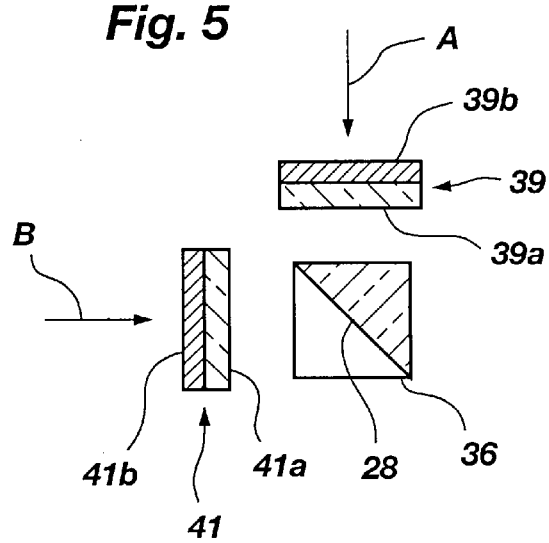
FIG. 5 is a schematic view of an alternative optical switching arrangement incorporating two optical valves.

An alternative design of the optical switching arrangement shown in FIGS. 2-3 is shown schematically in FIG. 5. Two optical switches 39 and 41 are positioned adjacent to the beam splitter 36 as shown. Arrow A represents the right image entering the optical switch 39, and arrow B represents the left image entering the optical switch 41. The left and right images are thereby alternated before entering the beam splitter 36, instead of after as in the embodiments of FIGS. 2-3. This alternative design offers better contrast and thus a higher quality stereoscopic view.

The method of use of the laparoscope 10 is quite simple. A physician makes a small incision in the abdominal cavity and inserts the distal end 11 of the laparoscope 10 therein so that said distal end resides within the abdominal cavity at a desired location. The physician can then inspect the location by viewing the three dimensional video image thereof displayed by the specialized glasses 58, rotating and otherwise maneuvering the laparoscope as desired in order to achieve an optimal view.

It is to be understood that scope of the invention includes replacing the fiber bundle 40 with any suitable image-carrying apparatus. For example, the bundle 40 could be replaced with a CCD camera chip as known in the art, allowing elimination of fiber bundles completely. This may prove advantageous, depending on the needs of the user. The smaller the CCD camera chip is, the more advantageous it becomes to substitute such a camera chip for the fiber bundle 40.

It is known in the art to rotate optical images electronically. The optical images produced in accordance with the present invention could be electronically rotated by 180 degrees, thereby allowing insertion of the laparoscope 10 from either side of a region to be viewed.

The present invention represents a significant advance over traditional apparatus and methods of stereoscopic viewing. It is noted that many of the advantages of the present invention accrue due to the placement of the observation windows in the side walls of the casing, and the combination of a relay lens system, an optical switch and a single light-transmitting and image-receiving fiber bundle within a conventional tubular casing. The problems associated with cost, weight, compactness and image quality are overcome to a significant degree by combination of an optical switch with a single fiberoptic bundle, and the placement of the observation windows in the side walls of the casing. Although the prior art apparatus and methods for stereoscopic viewing offer some of the advantages of fiberoptics and stereoscopic viewing, their disadvantages, including relatively high cost, weight and lack of compactness are overcome by the present invention's use of a single fiber bundle. Those skilled in the art will appreciate from the preceding disclosure that the objectives stated above are advantageously achieved by the present invention.

The embodiment of the invention as a surgical instrument is merely illustrative, and does not limit the scope of the present invention. For example, the invention may be applied to extend optical vision to any context or space where it desired that human contact therewith be avoided, such as in radioactive environments, in space or in deep sea applications. Any suitable size or configuration of the invention may be employed, and the optical imaging assemblies may in some applications be spaced six feet apart, for example.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A stereo laparoscope for producing a stereoscopic optical image of an intracorporeal region external to the laparoscope comprising:

a hollow casing;

means for illuminating the intracorporeal region to thereby cause said region to reflect light;

a plurality of observation openings disposed in the casing for receiving light reflected from the intracorporeal region;

a plurality of light imaging means disposed within the casing for processing the light received from the observation openings into left and right optical images of the intracorporeal region and transmitting said optical images to an image receiving means, said light imaging means comprising a first light imaging means and a second light imaging means;

image receiving means disposed in the casing for receiving the left and right optical images from the light imaging means and transmitting said images to an output display to thereby produce a stereoscopic optical image of the intracorporeal region on said output display;

variable depth perception means disposed in the casing for varying depth perception of the stereoscopic optical image;

wherein the plurality of light imaging means further comprises focusing means for varying focus of the left and right optical images, the stereo laparoscope further comprising:

synchronizing means for simultaneously varying (i) the depth perception of the stereoscopic optical image, and (ii) the focus of the left and right optical images.

2. The stereo laparoscope of claim 1, wherein the synchronizing means comprises an automated control means for varying the focus of the left and right optical images responsive to variation in the depth perception of the stereoscopic optical image.

3. The stereo laparoscope of claim 2, wherein the automated control means comprises an electro-mechanical means for producing an electrical signal corresponding to variation in the depth perception of the stereoscopic optical image, varying the focus of the left and right optical images responsive to said electrical signal.

4. The stereo laparoscope of claim 1, wherein the image receiving means defines at least one image plane, and wherein the first and second light imaging means further comprises first and second lenses respectively each lens having a focal length, and wherein the synchronizing means further comprises means for varying the depth perception and focus to thereby substantially maintain a mathematical relationship as follows:

$$1/f_1 = 1/l_1 + 1/l_2,$$

where $f_1$=the focal length of the lenses, $l_1$=working distance, defined as a distance between the lenses and the intracorporeal region, and $l_2$=image distance, defined as a distance between a lens and an image plane.

5. The stereo laparoscope of claim 1, wherein the casing comprises an elongate casing having sidewalls defining an axial direction, and wherein at least a first observation opening and a second observation opening are formed in said sidewalls, wherein the first and second light imaging means includes a first lens having a first optical axis and a second lens having a second optical axis respectively, said first and second lenses being disposed to face the first and second observation openings, respectively, such that the first and second optical axes extend transversely with respect to the axial direction of the casing, and wherein the image receiving means comprises a first image receiver disposed in alignment with the first lens and a second image receiver disposed in alignment with the second lens;

wherein the synchronizing means includes means for (i) moving the lenses in a substantially parallel direction relative to the axial direction of the casing, and (ii) moving the lenses in a transverse direction relative to the axial direction of the casing and thus toward and away from the image receivers.

6. The stereo laparoscope of claim 1, wherein the first and second light imaging means further comprises first and second lenses respectively separated by a separation distance, and wherein a working distance is defined as a distance between a lens and the intracorporeal region, and wherein the variable depth perception means further comprises:

means for varying the separation distance responsive to variation in the working distance, in a manner sufficient to maintain a substantially constant ratio of working distance to separation distance.

7. The stereo laparoscope of claim 1, wherein the first and second light imaging means further comprises first and second lenses respectively separated by a separation distance, and wherein the synchronizing means further comprises:

an automated control means for varying the focus of the left and right optical images responsive to variation in the separation distance between the first and second lenses.

8. The stereo laparoscope of claim 7, wherein the automated control means comprises an electro-mechanical means for producing an electrical signal corresponding to variation in the depth perception of the stereoscopic optical image, varying the focus of the left and right optical images responsive to said electrical signal.

9. The stereo laparoscope of claim 1, wherein the plurality of light imaging means and the image receiving means collectively comprise a first image processing assembly and a second image processing assembly, each image processing assembly comprising a lens and an image receiver, and wherein the variable depth perception means comprises a moving means for moving one of the image processing assemblies relative to the other image processing assembly.

10. The stereo laparoscope of claim 9, wherein the moving means comprises a manually operable means for moving one of the image processing assemblies relative to the other image processing assembly.

11. The stereo laparoscope of claim 1, wherein the first and second light imaging means further comprises first and second lenses respectively separated by a separation distance, and wherein the variable depth perception means further comprises:

means for (i) measuring a working distance, said working distance being defined as a distance between a lens and the intracorporeal region, and (ii) generating a signal corresponding to said working distance; and means responsive to the signal for varying the separation distance in a manner sufficient to maintain a substantially constant ratio of working distance to separation distance.

12. The stereo laparoscope of claim 1, wherein the image receiving means comprises first and second CCD camera chips.

13. The stereo laparoscope of claim 1, wherein the image receiving means comprises a single optical fiber bundle disposed within the casing and having a first end, a second end and fibers for receiving optical images at said first end.

14. The stereo laparoscope of claim 1, wherein the casing is elongate and defines an axial direction, said casing having sidewalls and wherein at least a first observation opening and a second observation opening are formed in said sidewalls;

wherein the first and second light imaging means further comprises first and second lenses respectively disposed within the casing and facing the first and second observation openings, respectively, said first and second lenses being configured and dimensioned to define first and second optical axes, respectively;

wherein the image receiving means comprises first and second image receivers disposed within the casing in alignment with the first and second optical axes, respectively.

15. The stereo laparoscope of claim 1, wherein the first and second light imaging means further comprises a first lens and a second lens respectively, said first and second lenses being configured and dimensioned to define first and second optical axes, said lenses being positioned and arranged such that their optical axes coincide substantially at the intracorporeal region to thereby define an acute angle.

16. The stereo laparoscope of claim 15, wherein the image receiving means comprises a first image receiver and a second image receiver disposed within the casing, said first and second image receivers respectively defining first and second image planes that reside in alignment with the first and second optical axes, and substantially perpendicular to said first and second optical axes.

17. The stereo laparoscope of claim 1, wherein the image receiving means includes a first image receiver and a second image receiver.

18. A stereo laparoscope for producing a stereoscopic optical image of an intracorporeal region external to the laparoscope comprising:

a hollow casing;

means for illuminating the intracorporeal region to thereby cause said region to reflect light;

a plurality of observation openings disposed in the casing for receiving light reflected from the intracorporeal region;

light imaging means disposed within the casing for processing the light received from the observation openings into left and right optical images of the intracorporeal region and transmitting said optical images to an image receiving means;

image receiving means disposed on the casing for receiving the left and right optical images from the light imaging means and transmitting said images to an output display to thereby produce a stereoscopic optical image of the intracorporeal region on said output display; and variable depth perception means disposed in the casing for varying depth perception of the stereoscopic optical image;

wherein the light imaging means further comprises focusing means for varying focus of the left and right optical images, the stereo laparoscope further comprising:

synchronizing means for simultaneously varying (i) the depth perception of the stereoscopic optical image, and (ii) the focus of the left and right optical images;

wherein the image receiving means defines at least one image plane, and wherein the light imaging means further comprises first and second lenses, each lens having a focal length, and wherein the synchronizing means further comprises means for varying the depth perception and focus to thereby substantially maintain a mathematical relationship as follows:

$$1/f_1 = 1/l_1 + 1/l_2,$$

where $f_1$=the focal length of the lenses, $l_1$=working distance, defined as a distance between the lenses and the intracorporeal region, and $l_2$=image distance, defined as a distance between a lens and an image plane;

wherein the casing comprises an elongate casing having sidewalls defining an axial direction, and wherein at least a first observation opening and a second observation opening are formed in said sidewalls, wherein the light imaging means includes a first lens having a first optical axis and a second lens having a second optical axis, said first and second lenses being disposed to face the first and second observation openings, respectively, such that the first and second optical axes extend transversely with respect to the axial direction of the casing, and wherein the image receiving means comprises a first image receiver disposed in alignment with the first lens and a second image receiver disposed in alignment with the second lens;

wherein the synchronizing means includes means for (i) moving the lenses in a substantially parallel direction relative to the axial direction of the casing, and (ii) moving the lenses in a transverse direction relative to the axial direction of the casing and thus toward and away from the image receivers;

wherein the light imaging means further comprises first and second lenses separated by a separation distance, and wherein a working distance is defined as a distance between a lens and the intracorporeal region, and wherein the variable depth perception means further comprises:

means for varying the separation distance responsive to variation in the working distance, in a manner sufficient to maintain a substantially constant ratio of working distance to separation distance;

wherein the image receiving means comprises first and second CCD camera chips;

wherein the lenses are positioned and arranged such that the first and second optical axes coincide substantially at the intracorporeal region to thereby define an acute angle;

wherein the image receiving means comprises a first image receiver and a second image receiver disposed within the casing, said first and second image receivers respectively defining first and second image planes that reside in alignment with the first and second optical axes, and substantially perpendicular to said first and second optical axes.

19. A method of producing a stereoscopic optical image of an intracorporeal region, said method comprising the steps of:

(a) inserting a casing into a body and illuminating the intracorporeal region to thereby cause said region to reflect light;

(b) processing light reflected from the intracorporeal region into left and right optical images and transmitting said optical images within the casing to an image receiving means disposed within said casing;

(c) transmitting said optical images to an output display to thereby produce a stereoscopic optical image of the intracorporeal region on said output display; and (d) varying depth perception of the stereoscopic optical image;

(e) simultaneously varying the depth perception of the stereoscopic optical image and focusing the left and right optical images.

20. The method of claim 19, wherein step (b) further comprises using a first lens and a second lens to process the light, each lens having a focal length, and wherein step (c) further comprises using a first image receiver and a second image receiver to produce the stereoscopic optical image, each image receiver defining an image plane, and wherein step (d) further comprises varying the depth perception and focus to thereby substantially maintain a mathematical relationship as follows:

$$1/f_1 = 1/l_1 + 1/l_2,$$

where $f_1$=the focal length of the lenses, $l_1$=working distance, defined as a distance between the lenses and the intracorporeal region, and $l_2$=image distance, defined as a distance between a lens and an image plane.

21. The method of claim 19, wherein step (b) further comprises using a first lens and a second lens to process the light, said first and second lenses being separated by a separation distance, and wherein a working distance is defined as a distance between a lens and the intracorporeal region, and wherein step (d) further comprises varying the separation distance responsive to variation in the working distance, in a manner sufficient to maintain a substantially constant ratio of working distance to separation distance.

* * * * *